United States Patent [19]

Abramson

[11] Patent Number: 5,161,543
[45] Date of Patent: Nov. 10, 1992

[54] APPARATUS FOR MONITORING STOMACH MUSCLE CONDITION

[76] Inventor: Kanan E. Abramson, 834 Chestnut St., Apt. 1606, Philadelphia, Pa. 19107

[21] Appl. No.: 592,584

[22] Filed: Oct. 4, 1990

[51] Int. Cl.$^5$ .............................. A61B 5/103
[52] U.S. Cl. ...................... 128/774; 33/512
[58] Field of Search ............... 128/780–782, 128/774, 845; 33/511, 512; 606/57

[56] References Cited

U.S. PATENT DOCUMENTS

| | | | |
|---|---|---|---|
| 3,582,935 | 6/1971 | Verhaeghe | 128/781 |
| 3,608,541 | 9/1971 | Hall | 128/781 |
| 3,991,745 | 11/1976 | Yoslow et al. | 128/781 |
| 4,007,733 | 2/1977 | Celeste et al. | 128/781 |
| 4,312,363 | 1/1982 | Rothfuss et al. | 128/774 |
| 4,730,625 | 3/1988 | Fraser et al. | 128/781 |

FOREIGN PATENT DOCUMENTS

| | | | |
|---|---|---|---|
| 2205039 | 11/1988 | United Kingdom | 128/781 |
| 0011247 | 11/1989 | World Int. Prop. O. | 128/781 |

*Primary Examiner*—Max Hindenburg

[57] ABSTRACT

One of its aspects this invention provides a simple stomach muscle condition monitoring apparatus. The apparatus includes a spine which encompasses a first longitudinally elongated base member, having a first, free end and a tongue longitudinally extending from the second, remaining end, and a second longitudinally elongated base member having a first free end and a longitudinally extending slot in the second, remaining end. The slot receives the first base member tongue. Means are provided to secure the tongue in the slot at various longitudinal positions thereby permitting the longitudinal length of the spine to be adjustably varied. Sensing means, preferably pressure sensor means, connects to the spine and is preferably positioned transversely to the longitudinal axis of the spine's two base members. An alarm connected to the sensing means produces a signal upon actuation of the senors; the sensor may also (or alternatively) actuate a remote recorded message or instructions for the user. Spacer means attach to the free ends of the first and second base members, and preferably face in the same direction as the sensing means for contact with the body.

16 Claims, 5 Drawing Sheets

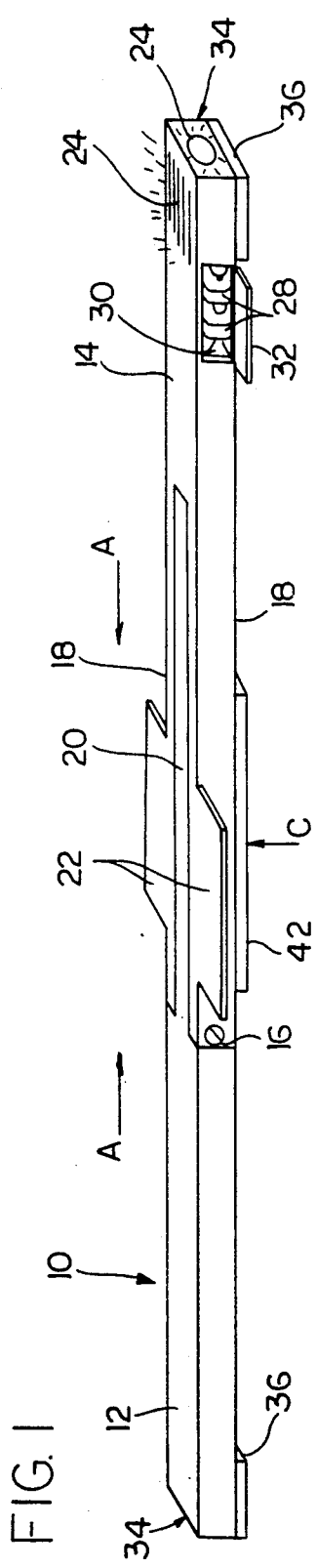
FIG. 1
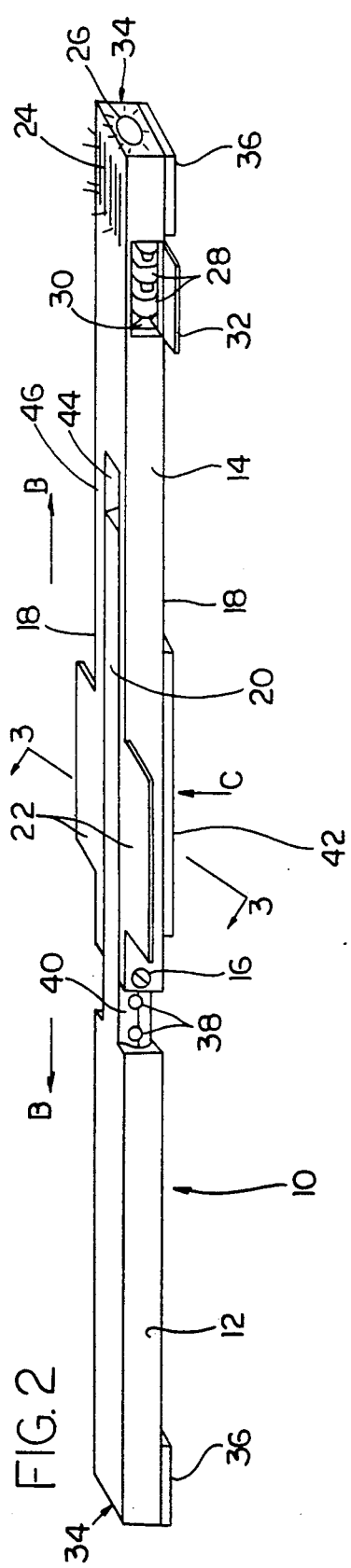
FIG. 2
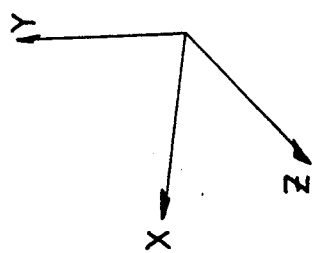

APPARATUS FOR MONITORING STOMACH MUSCLE CONDITION

BACKGROUND OF THE INVENTION

This invention provides a method and apparatus for measuring and monitoring stomach protrusion.

FIELD OF THE INVENTION

Physical fitness awareness results in people desiring to maintain their stomach in a "flat" condition. Lack of exercise typically leads to poor muscle tone, resulting in unwanted stomach protrusion. Advancing age also contributes to this, as does occasional stomach muscle disorder. Accordingly, it is desirable to provide a device and method capable of measuring proper stomach muscle condition as reflected by stomach protrusion or lack thereof.

DESCRIPTION OF THE PRIOR ART

Applicant is aware of the following U.S. Pat. Nos. qualifying as prior art respecting this invention: 2,324,672; 3,582,935; 3,608,541; 3,637,207; 3,908,279; 3,945,373; 4,122,837; 4,392,126; 4,485,825; 4,696,307; and 4,730,652. The most relevant are 3,945,373 and 4,696,307, with '307 being the more relevant.

'307 discloses a device for measuring stomach movement. The device consists of a housing attached to the subject's stomach by straps. The housing has a displacement transducer, thrusters and a pressure spring. A ring carries an adhesive lining to assist in keeping the housing in a desired location about the stomach. Displacement of the thruster resulting from stomach movement completes an electronic circuit that actuates light and sound sources.

SUMMARY OF THE INVENTION

One of its aspects this invention provides a simple stomach muscle condition monitoring apparatus. The apparatus includes a spine which encompasses a first longitudinally elongated base member, having a first, free end and a tongue longitudinally extending from the second, remaining end, and a second longitudinally elongated base member having a first free end and a longitudinally extending slot in the second, remaining end. The slot receives the first base member tongue. Means are provided to secure the tongue in the slot at various longitudinal positions thereby permitting the longitudinal length of the spine to be adjustably varied. Sensing means, preferably pressure sensor means, connects to the spine and is preferably positioned transversely to the longitudinal axis of the spine's two base members. An alarm connected to the sensing means produces a signal upon actuation of the senors; the sensor may also (or alternatively) actuate a remote recorded message or instructions for the user. Spacer means attach to the free ends of the first and second base members, and preferably face in the same direction as the sensing mean for contact with the body.

In another of its aspects the invention provides a method for monitoring human stomach muscle condition. The method includes locating the pubic bone of a human subject and contacting the skin exterior of the bone with a spine component member. The method further includes locating the bottom tip of the breast bone and contacting the skin exterior thereof with a second spine component member. The spine, having a sensing device and an alarm, connects to the spacers; the sensing device is located to contact the stomach upon the stomach muscles relaxing. Once the spine member is been applied to the spacers, the subject relaxes the stomach, permitting the stomach to protrude outwardly towards the sensing device. If the stomach contacts the sensing device, an alarm activates.

In yet another of its aspects, this invention provides a caliper-like device, which may be located on one end of the apparatus or may be free-standing, for monitoring human stomach muscle condition, where the caliper has a pair of lips. One of the caliper lips is preferably integrally formed on the end of the apparatus for monitoring human stomach muscle condition and the other of the lips movable respecting the first lip. The movable lip is connected to a tongue-like piece which is movable within a groove formed in the main portion of the apparatus for monitoring human stomach muscle condition. The groove is preferably a longitudinal groove and is preferably formed in the base or spine member on the side thereof opposite (considered respecting the outwardly facing direction) from the alarm surface.

Further provided are indicia, preferably in both centimeters and inches, for measuring the distance between the two lips, thereby providing a measurement of the thickness of the fat layer between the belly muscles and the skin The positioning of the caliper lips is such that the lips do not contact the body when using the apparatus. The caliper is preferably located oppositely from a foot member which faces the spine member from the body. The caliper may be detachable from the main apparatus.

DESCRIPTION OF THE DRAWINGS

FIG. 1 is a perspective view of a preferred embodiment of a stomach muscle monitoring instrument in accordance with one aspect of the invention.

FIG. 2 is a perspective view of the instrument shown in FIG. 1 illustrated in an extended position in accordance with one aspect of the invention.

DETAILED DESCRIPTION OF THE INVENTION

Figure 4:
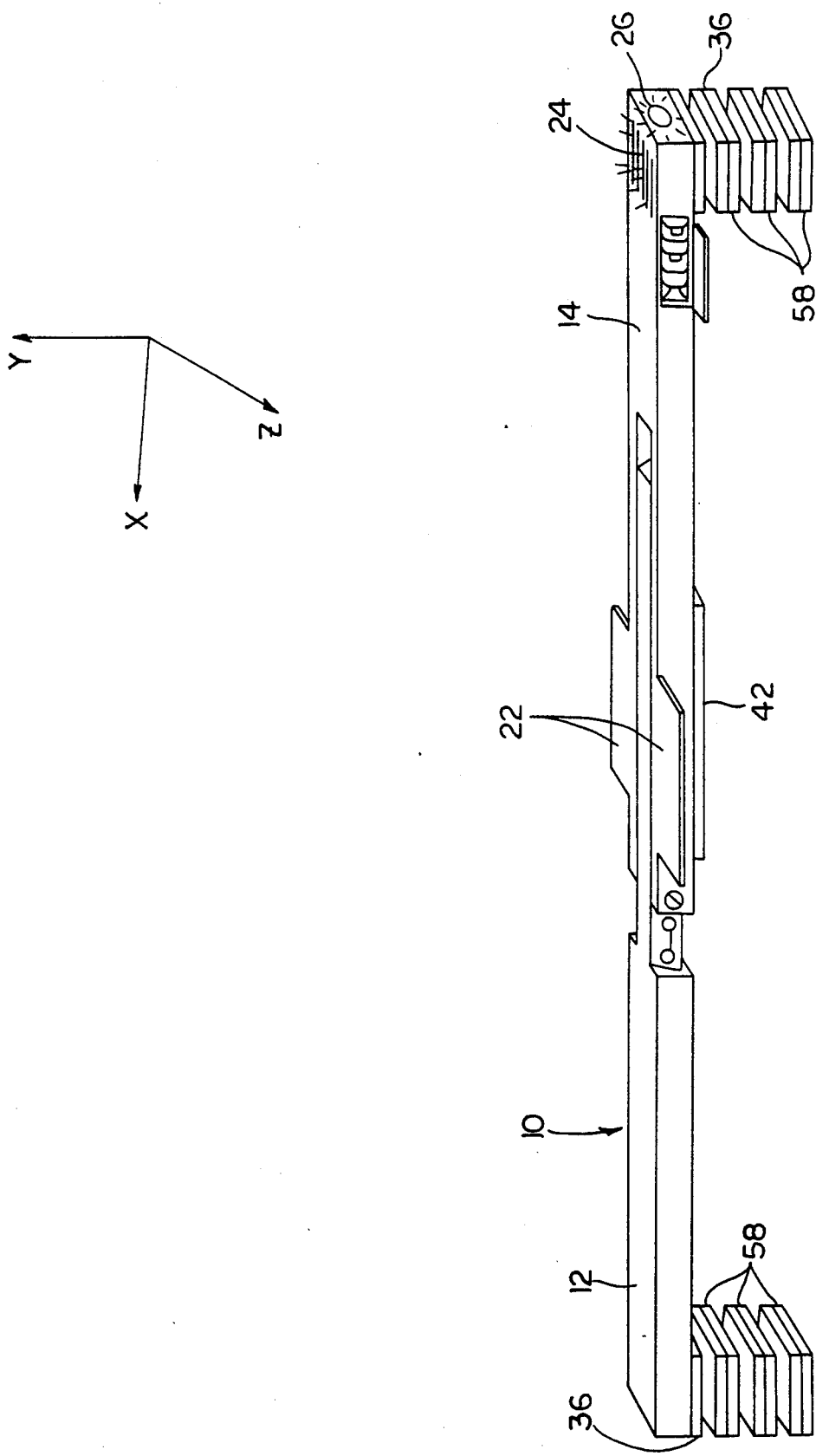
FIG. 4 is a perspective view of another embodiment of the instrument having additional pairs of extension feet, with the feet illustrated as broken apart for drawing clarity.

FIGS. 2 and 4 have directional axes labelled "x", "y" and "z". In the description of the invention, the "x" axis is generally referred to as the longitudinal axis and as defining a longitudinal direction. These axes are referred to throughout this description and assist in understanding the invention. The axes are not intended to limit the scope of the claims.

Referring to the drawings in general and to FIGS. 1 and 2 in particular, a stomach muscle monitor 10 includes first longitudinally elongated base member 12 and second longitudinally elongated base member 14, which together define a longitudinally extending spine and are connected together by length adjustment screw 16. Screw 16 extends through a pair of second base member arms 18 and tongue 20 which extends outwardly from first base member 12.

Each arm 18 has a gripping handle 22 extending outwardly in a direction (as shown by directional axis z) transverse t the longitudinal axis of first and second base members 12 and 14. Second base member 14 has buzzer 24 and red light 26 powered by batteries 28. Batteries 28 reside within housing 30 and are accessible by door 32. The remote ends 34 of first and second base members 12 and 14 have feet 36 mounted thereto and extending in a direction (parallel to axis y) perpendicular to the longitudinal axis (defined by longitudinal axis x) of first and second base members 12 and 14.

First base member 12 has multiplicity of screw holes extending through tongue 20, with the openings of holds 38 lying along sidewalls 40 of tongue 20. Release of length adjustment screw 16 permits longitudinal sliding movement of first and second base members 12 and 14 with respect to one another.

FIG. 1 shows monitor 10 in a "closed" configuration, with the first and second base members 12 and 14 closely longitudinally aligned with respect to one another as shown by the arrows labelled "A". FIG. 2 shows monitor 10 in an "open" configuration, with arrows "B" representing longitudinal sliding displacement of base members 12 and 14 from one another. Movement represented by arrows A and B occurs along sidewalls 40 and 46.

Figure 3:
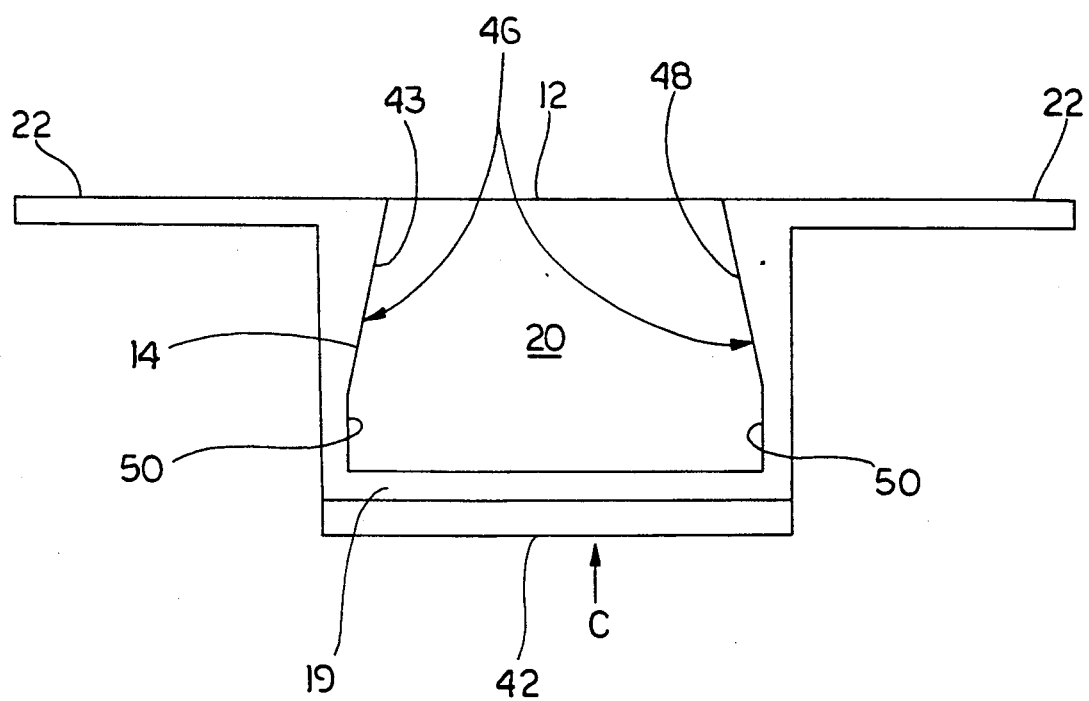
FIG. 3 is a vertical schematic cross-sectional view of the instrument taken at lines and arrows 3—3 in FIG. 2.

Sensor 42 connects to the underside of monitor 10 along floor 19, shown in FIG. 3, of second base member 14. Floor 19 connects second base member arms 18 together.

Referring to FIG. 3, sidewalls 46 of arms 18 have beveled portions 48 and vertical portions 50. Vertical portions 50 connect to floor 19. Pressure sensor 42 is mounted in floor 19 preferably close to the longitudinal middle of monitor 10, close to the end of second base member 14 opposite remote end 32, in the vicinity of slot 44.

Pressure sensor 42 connects to a buzzer or to a recording device 24, red light 26 and batteries 28 by a conventional circuit. Application of force to pressure sensor 42 in the general direction shown by arrow C activates the buzzer and/or recording device 24 and/or preferably red light 26.

FIG. 4 shows monitor 10 with multiple pairs of extension feet 58 attached to feet 36.

Figure 7:
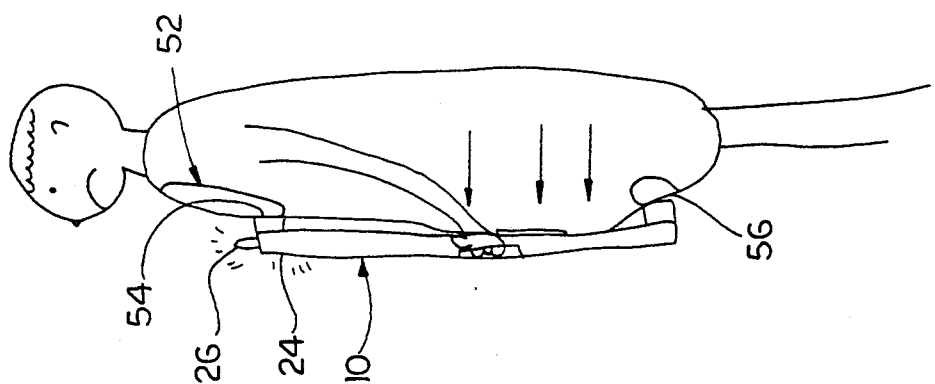
FIG. 7 is a schematic side view similar to FIGS. 5 and 6 after relaxation of the stomach, when the stomach protrudes outwards. In this position the alarm activates.
Figure 6:
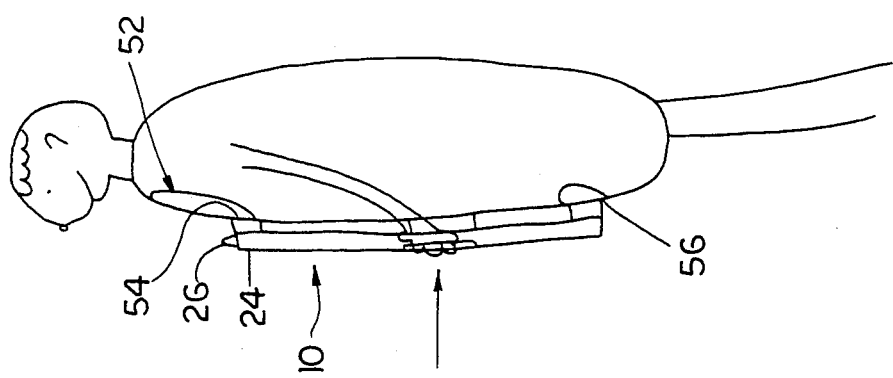
FIG. 6 is a schematic side view similar to FIG. 5, but after application to a test subject whose stomach is straight.
Figure 5:
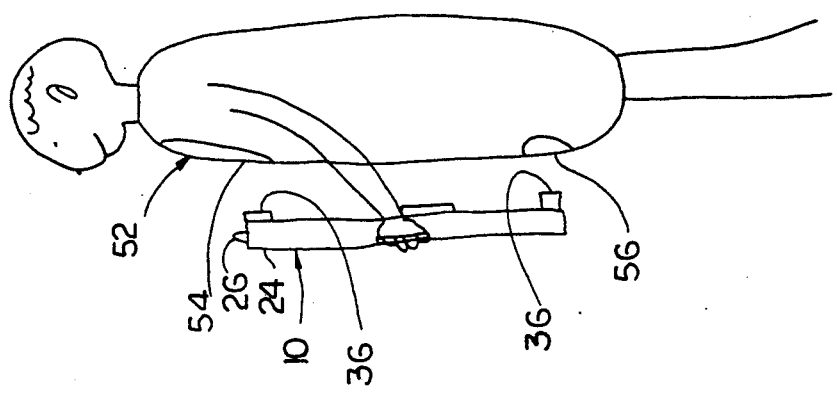
FIG. 5 is a schematic side view of the instrument prior to application to a test subject.

FIGS. 5 through 7 illustrate the method of use of monitor 10. As shown in FIG. 5, a subject wishing to measure protrusion of the stomach grips monitor 10 with handles 22 and holds monitor 10 substantially vertically in front of the subject's body. The subject then determines the location of the bottom portion of the breast bone and the location of the pubic bone and adjusts the length of monitor 10 by withdrawing length adjustment screw 16, longitudinally moving first and second base members 12 and 14 with respect to each other and inserting screw 16 in the proper hole 38 to extend monitor 10 to a length such that one foot 36 is in a position capable of touching the bottom portion of the breast bone and the other foot 36 lies in a position to contact the pubic bone. This is shown in FIG. 5.

Once the proper length of monitor 10 has been established and monitor 10 has been appropriately positioned, the subject relaxes the stomach and applies feet 36 to the lower portion 54 of breast bone 52 and to pubic bone 56 respectively. (It is also possible to first apply monitor 10 to lower portion 54 of breast bone 52 and to pubic bone 56 and then to relax the stomach ) If the subject's muscles are in good condition, the relaxed stomach will not extend too far outwardly and will not exert force against pressure sensor 42. Hence, the buzzer and/or the recording device 24 and/or the red light 26 are not activated. This is shown in FIG. 6.

If, upon application of monitor 10, the stomach protrudes outwardly too far, the stomach applies force against pressure sensor 42, thereby activating the buzzer and/or recording device 24 and/or the red light 26. This is shown in FIG. 7.

Activation of the buzzer and/or recording device 24 and/or the red light 26 indicates the subject should correct the stomach condition, by a particular exercise regimen and/or altered diet.

Monitor 10 can be used in a regular program of reduction of stomach protrusion by applying pairs of extension feet 58 to feet 36 as shown in FIG. 4. Application of extension feet 58 to feet 36 provides a greater distance that the stomach may protrude before contacting pressure sensor 42. A subject engaged in an exercise regimen or altered diet may begin the program with multiple pairs of extension feet 58 applied to monitor 10. Over time, as the subject progresses in the program by reducing stomach protrusion, pairs of extension feet 58 may be removed from monitor 10 to indicate progress made and progress yet to be made. The failure of the buzzer and/or the recording device 24 and/or the light 26 to activate indicates that the stomach does not extend outwardly far enough to contact pressure sensor 42. At that time one pair of extension feet 58 may be removed.

Figure 8:
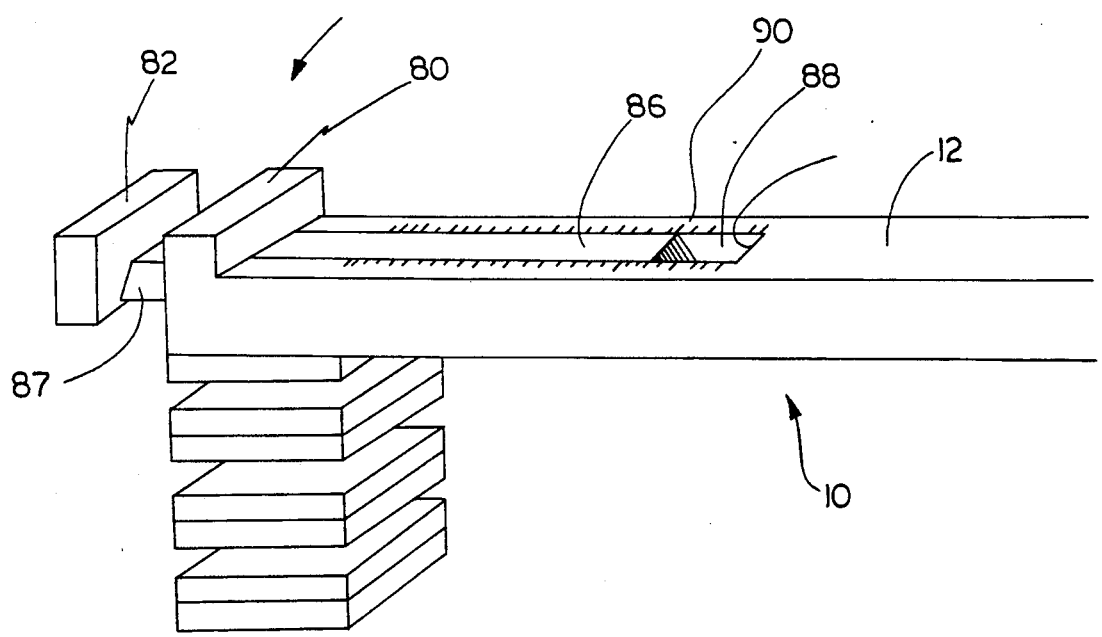
FIG. 8 is a broken perspective view, similar to that of FIGS. 1, 2 and 4, showing the caliper aspect of the invention.

Referring to FIG. 8, the two lips of the preferred embodiment of the caliper portion of the invention are denoted 80 and 82 respectively. Lip 80 is preferably integral with the spine portion or first base member 12 and lip 82 is movable respecting lp 80. The caliper portion of the invention is designated generally 84.

Movable lip 82 is formed integrally with a tongue portion 86 fitting within a groove 88 formed in base member 12. Tongue 86 is longitudinally slideable within groove 88 from a position at which a butt end 90 of tongue 86 is in flush facing contact with a bottom terminus 92, defining one end of groove 88 remote from fixed lip 80. In its preferred form, groove 88 is tapered somewhat in the transverse direction for flush fitting with side walls 87 of tongue 86, which are similarly tapered, at the same angle. The taper of side walls 87 is illustrated in FIG. 8.

Fixed lip 80 overlies groove 88, thereby retaining tongue 86 in position and preventing tongue 86 from falling out of groove 88.

Preferably imprinted on the surface of member 12, in which groove 88 is formed, are indicia, in both centimeters and inches, which permit the user to measure displacement of movable lip 82 from fixed lip 80 thereby measuring the thickness of the fat layer. The indicia may be either embossed on or engraved into the surface of member 12. The indicia are preferably positioned so as to permit measurement by determining the position of butt end 90 relative to the bottom 92 of groove 88. As illustrated in FIG. 8, when movable lip 82 is displaced from fixed lip 80, butt end 90 of tongue 86 is removed from bottom 92 of groove 88 a distance corresponding to separation of the lips. The user determines the displacement of the lips, after closing the lips towards each other and trapping the fat layer therebetween, by merely looking at the position of butt end 90 and seeing the distance measurement indicia line with which butt end 90 aligns.

The geometry of lips 80, 82 is not significant; the lips may be rectangular, square, round, oval or any other shape. A square or rectangular configuration is preferable.

In the preferred embodiment of the invention, lips 80, 82 are each about one-eighth to one-fourth inch thick. Groove 88 is preferably up to about three inches long, permitting the lips to be separated by as much as about three inches, thereby accommodating persons with large amounts of fat. Movement of tongue 86 within groove 88 permits lips 80, 82 to be spaced up to about three inches apart in the preferred embodiment of this invention. This is more than adequate for all but the most obese persons.

Lip 80 is preferably raised in the transverse direction on the facing surface of member 12 at least one-half inch and most preferably even a little more, to assure good measurement of the fat layer and to assure that the entire fat layer is encompassed between the lips during measurement. Between one-half inch and one inch elevation of fixed lip 80 respecting the facing surface of movable member 12 is preferable.

Because member 12 is preferably plastic, lips 80, 82, tongue 86, groove 88 and the associated structure can be easily formed during the molding process. Inexpensive fabrication is one advantage associated with this portion of the invention.

Referring again to FIGS. 1 and 2 of the drawings, the preferred monitor 10 is preferably dimensioned as follows:

(1) Total length of monitor 10 in the "closed" position as shown in FIG. 1 is about 12 inches.
(2) Length of monitor 10 in an "open" position as shown in FIG. 2 is about 16 inches.
(3) Thickness of first and second base members 12 and 14 is about three quarters of an inch.
(4) Total length of second base member 14 is about 9 inches.
(5) Pressure sensor 42 is about 3 inches long by one half inch wide by one eighth inch thick.
(6) Feet 36 and extension feet 58 are about one inch long by one inch wide by one eighth inch thick.
(7) Gripping handles 22 are about three inches long by three quarter inches wide by one sixteenth inch thick.
(8) Length of tongue 22 is about five inches.

Although the above dimensions are preferred, variations in length, width and height are possible. Also, monitor 10 may be constructed of a variety of materials, including wood, metals and plastics. First and second base members 12 and 14 may be solid or hollow.

Feet 36 and extension feet 58 may be constructed of any suitable material, such as wood, metals, plastic or rubber. Also, feet 36 may be connected to first and second base members 12 and 14 by any suitable means such as adhesives, screws, welds, etc. Extension feet 58 may also be attached in a variety of manners, but it is preferred that the attachment means be easily removable and reconnectable. Options include (1) clips that attach to feet 36 or interior extension feet 58 or (2) extension feet 58 may be constructed of magnetic material that adheres to feet 36 or other extension feet 58, for example. Other options are also possible.

Pressure sensor 42 is preferably a flexible rubber material covering a spring loaded activation device. However, other pressure sensitive devices may be used. Also, pressure sensor 42 may be connected to either or both buzzer 24 and red light 26 and batteries 28 in a known manner. It is not critical to the invention that the buzzer and recording device 24 and red light 26 all be present It is only important that some device be utilized to signal that the subject's stomach muscles have extended outwardly too far beyond a desired point and have contacted pressure sensor 42.

While gripping handles 22 have been shown extending in the direction of directional axis z, this is not critical to the invention. Gripping handles 22 may extend in other directions and may be constructed in different configurations. It is also possible to construct monitor 10 without handles 22, although gripping handles 22 are preferred.

I claim the following:

1. Stomach monitoring apparatus comprising:
   (a) a first elongated base member having a free end and a tongue longitudinally extending from the other end;
   (b) a second elongated base member having a free end and a longitudinally extending slot in the other end, said slot being sized to receive said tongue from said first base member;
   (c) means for connecting said tongue and said slot at varying longitudinal positions;
   (d) pressure sensor means connected to one of said base members and positioned normal to an axis extending along said base members;
   (e) alarm means connected to said pressure sensor means and capable of producing a signal or recording upon application of force to said pressure sensor means; and
   (f) feet attached to free ends of said first and second base members, said feet facing in the same direction as said pressure sensor means.

2. Apparatus as defined in claim 1 further comprising handle attached to said second base member along said slot.

3. Apparatus as defined in claim 1 wherein said means for connecting comprises an adjustment screw.

4. Apparatus as defined in claim 1 wherein said pressure sensor means comprises a piece of flat flexible rubber extending over a spring electrically connected to said alarm means.

5. Apparatus as defined in claim 1 wherein said alarm is battery powered.

6. Apparatus as defined in claim 1 wherein said alarm is a buzzer and/or recording means.

7. Apparatus as defined in claim 1 wherein said alarm is a light.

8. Apparatus as defined in claim 1 further comprising one or more pairs of extension feet connected to said feet.

9. Apparatus as defined in claim 1 further comprising a pair of opposed ridges extending along said tongue and engaging a pair of opposed grooves in said second base member along said slot, said ridges and grooves permitting lengthening and shortening sliding movement of said base members along said axis.

10. A stomach monitor comprising:

(a) a flat elongated body having a necked down portion on one end;
(b) a second elongated body having a cavity in one end;
(c) connection means for slidable, releasably connecting said necked down portion and said cavity;
(d) pressure sensitive means mounted to one of said bodies in a direction perpendicular to the direction of the slidability of said bodies;
(e) an alarm and/or recording connected to said pressure sensitive means activated in response to force applied to said pressure sensitive means; and
(f) leg members attached to said bodies and positioned to face in the same direction as said pressure sensitive means.

11. A stomach monitor comprising:
(a) a first elongated housing having one free end and a necked down portion on the other end, said necked down portion having a pair of elongated opposed ridges;
(b) a second elongated housing having one free end and a channel on the other end, said second housing also having a pair of elongated grooves extending along walls forming said channel;
(c) removable connection means insertable into a multiplicity of spaced apart holes in said necked down portion and said walls to permit sliding action of said housing along said ridges and grooves of said necked down portion and said channel respectively;
(d) pressure sensitive means fixed to one of said housing in a direction perpendicular to the direction of the slidability of said housing and including a spring covered with flexible rubber;
(e) an alarm/recording means electrically connected to said pressure sensitive means and mounted to one of said housing activatable in response to force applied to said pressure sensitive means; and
(f) leg member attached to said housings and positioned to face in the same direction as said pressure sensitive means.

12. Stomach monitoring apparatus comprising:
(a) a longitudinally elongatable base;
(b) means for fixing said base at varying longitudinal elongations;
(c) means connected to said base for sensing external contact therewith in a direction substantially normal to the longitudinal axis;
(d) alarm means connected to said contact sensing means for producing a signal upon external agency contact with said sensing means; and
(e) feet attached to the ends of said base, said feet facing substantially in a direction of external contact of said sensing means.

13. Apparatus of claim 12 further comprising:
(a) a longitudinally extending groove formed in one end of said longitudinally-elongatable base;
(b) a tongue slideably movable longitudinally within said groove;
(c) a lip member at the end of said base within which said groove is formed; said lip member overlying said groove;
(d) a second lip upstanding from said tongue, adapted for complemental facing contact with said first lip upon movement of said tongue within said groove.

14. Apparatus of claim 13 further comprising indicia on said base member adjacent said groove for measuring longitudinal displacement of said tongue relative to said groove, thereby providing indirect measurement of displacement of said lips one from another.

15. Apparatus of claim 14 wherein when said lips are in complemental facing contact, a butt end of said tongue remote from said movable lip abuttingly contacts an end of said groove remote from said end of said base at which said groove is formed.

16. Apparatus for measuring thickness of fat between stomach muscles and the skin, comprising:
(a) a base;
(b) a transversely tapered longitudinally extending transversely open groove formed at one end of said base;
(c) a longitudinally elongated transversely tapered tongue facingly contacting said groove and freely slideably movable longitudinally within and longitudinally removable from said groove;
(d) a longitudinally elongated transversely extending lip member at an end of said base within which said open groove is formed, said lip member partially overlying said open groove;
(e) a longitudinally elongated second lip generally transversely extending upstanding from said tongue, adapted for complemental longitudinally sliding facing contact with said first lip upon longitudinal movement of said tongue within said groove; and
(f) indicia on said base adjacent said groove for measuring longitudinal displacement of said tongue relative to said groove, thereby providing indirect measurement of longitudinal displacement of said lips one from another.

* * * * *